US007014794B1

(12) United States Patent  
Olinga et al.

(10) Patent No.: US 7,014,794 B1  
(45) Date of Patent: Mar. 21, 2006

(54) USE OF SULPHONIC AND PHOSPHONIC ACIDS AS DOPANTS OF CONDUCTIVE POLYANILINE FILMS AND CONDUCTIVE COMPOSITE MATERIAL BASED ON POLYANILINE

(75) Inventors: Thomas Olinga, Bordeaux (FR); Adam Pron, Grenoble (FR); Jean-Pierre Travers, Martin d'Heres (FR)

(73) Assignee: Commissariat a l'Energie Atomique and Centre National de la Recherche Scientifique, (FR)

(*) Notice: Subject to any disclaimer, the term of this patent is extended or adjusted under 35 U.S.C. 154(b) by 238 days.

(21) Appl. No.: 10/030,584

(22) PCT Filed: Jul. 12, 2000

(86) PCT No.: PCT/FR00/02017

§ 371 (c)(1),  
(2), (4) Date: Jan. 9, 2002

(87) PCT Pub. No.: WO01/04910

PCT Pub. Date: Jan. 18, 2001

(30) Foreign Application Priority Data

Jul. 13, 1999 (FR) .................................. 99 09088

(51) Int. Cl.  
*H01B 1/12* (2006.01)  
*H01B 1/20* (2006.01)  
*B32B 5/00* (2006.01)

(52) U.S. Cl. ...................... 252/500; 252/511; 252/519; 252/521; 428/357; 428/370; 428/407

(58) Field of Classification Search ................ 252/500, 252/511, 518, 521; 428/357; 525/185, 186, 525/191

See application file for complete search history.

(56) References Cited

U.S. PATENT DOCUMENTS

| 2,828,326 | A |   | 3/1958  | Doerr et al. |
| 3,088,956 | A |   | 5/1963  | Horn et al. |
| 4,500,680 | A |   | 2/1985  | Singer et al. |
| 5,585,040 | A | * | 12/1996 | Kirmanen et al. ..... 252/519.33 |
| 5,783,111 | A | * | 7/1998  | Ikkala et al. ................ 252/500 |
| 5,908,898 | A | * | 6/1999  | Wan-Cheng et al. ........ 525/185 |
| 6,235,220 | B1 |  | 5/2001  | Pron et al. |

FOREIGN PATENT DOCUMENTS

| CA | 2119518     |   | 3/1994  |
| EP | 0 615 973   |   | 9/1994  |
| JP | 08-041322   | * | 2/1996  |
| JP | 08041322    | A * | 2/1996  |
| JP | 08-100060   | * | 4/1996  |
| JP | 08-120167   | * | 5/1996  |
| JP | 10339931    |   | 12/1998 |
| WO | WO 98/05040 |   | 2/1998  |

OTHER PUBLICATIONS

Bajer et al, "Spectroscopic Studies of polyaniline protonated with esters of 5-isophthalic acid,", 1999, 101, pp 713-714.*  
Grodzinsky, "Electronically Conductive Polymers," Polym. Adv. Technol. 2002, 13, pp 615-625.*  
XP-000901311—P.D. 1857, pp. 239 to 264B.  
XP-000891529—P.D. 1921, pp. 724 to 735.  
XP-002134949—P.D. Nov. 5, 1962, pp. 1703 to 1709.  
XP-002134948—P.D. Jun. 1966, pp. 241 to 247.  
XP-002134950—P.D. Mar. 18, 1974, p. 338.  
XP-002134946—P.D. 1974, pp. 3735 to 3738.  
POLYMER, 1993, vol. 34, No. 20—pp. 4235 to 4240.  
Synthetic Methals, 48-1992, pp. 91 to 97.  
J. Chem. Phys. vol. 103, No. 22—Dec. 8, 1995, pp. 9855 to 9863.  
Characterization of Sulfonic Acid Doped Polyaniline Processed From Hexafluorolsopropanol, pp. 396 to 397.  
J. Phys.: Condens. Matter Oct. 1998, pp. 8293 to 8903.  
Physical Review B, Condensed Matter, Third Series, vol. 50, No. 19—Nov. 15, 1994-I, pp. 13931 to 13941.  
Synthetic Metals 95—1998, pp. 29 to 45.  
Synthetic Metals—1999, pp. 713 to 714 XP000195647—P.D. 1992, pp. 91 to 97.  
XP-002134947—P.D. May 17, 1995, pp. 2707 to 2710.  
Synthetic Metals, 21—1987, pp. 21 to 30.

* cited by examiner

*Primary Examiner*—Mark Kopec  
*Assistant Examiner*—Kallambella Vijayakumar  
(74) *Attorney, Agent, or Firm*—Anderson Kill & Olick, PC

(57) ABSTRACT

The present invention concerns the use of sulphonic and phosphonic acids, functionalised with plastisizers, as dopants for polyaniline conductor films and polyaniline-based conductive composite materials.

These acids meet the following formula:

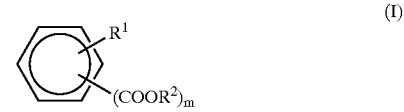

in which:  
$R^1$ represents —$SO_3H$ or $PO_3H_2$  
$R^2$ is a linear or branched alkyl group and m equals 1 or 2, or  
$R^2$ is a group having the formula:

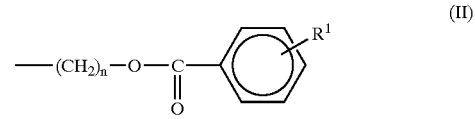

in which $R^1$ is such as defined above and n is a whole number ranging from 1 to 16, and m equals 1.

24 Claims, 1 Drawing Sheet

US 7,014,794 B1

USE OF SULPHONIC AND PHOSPHONIC ACIDS AS DOPANTS OF CONDUCTIVE POLYANILINE FILMS AND CONDUCTIVE COMPOSITE MATERIAL BASED ON POLYANILINE

TECHNICAL FIELD

The present invention concerns the use of sulphonic and phosphonic acids as dopants for polyaniline-based electricity conductive materials.

More precisely, it concerns the manufacture of highly conductive polyaniline films having good mechanical properties, able to be used either in the form of thin films deposited on an appropriate substrate, or in the form of self-supporting films.

It also concerns the manufacture of conductor composite materials containing polyaniline and an insulating polymer.

These polyaniline films and films of polyaniline-based materials may be used for electromagnetic shielding, as antistatic materials or as semi-transparent electrodes in optoelectronic devices.

PRIOR ART

Generally, conductor polyaniline films are prepared from a solution of polyaniline in an organic solvent by pouring the solution and evaporating the solvent. To obtain a conductor film, the polyaniline needs to be conductive. However, polyaniline is generally obtained in its basic form which is not conductive, and it is therefore necessary to convert this basic form into a conductive protonated form, either before preparation of the film of after its manufacture.

This conversion may be obtained using an appropriate dopant, generally an acid to cause the polyaniline to undergo a protonation reaction.

The protonation of polyaniline, after obtaining the film, is a complication that is hardly acceptable from an industrial viewpoint. Moreover, it is difficult to obtain a homogeneous product in this case since protonation is conducted in the solid state.

A further problem encountered for the preparation of polyaniline films resides in the fact that polyaniline is a polymer that is both infusible and very difficult to dissolve.

Document [1]: Synthetic Metals, 21, 1987, pp. 21–30, illustrates the use of acetic acid with a polyaniline in emeraldine form to prepare a solution of protonated polyaniline which can lead to the formation of polyaniline films through evaporation of the solvent.

However the films obtained from these solutions are scarcely conductive (0.5 at 2 S/cm) and have very poor mechanical properties. In addition, they ill withstand deprotonation which causes a sharp drop in the conductivity of the polymer.

Reference [2]: Polymer, 34, N° 20, 1993, pp. 4235–4240, illustrates the use of diesters of phosphoric acids to protonate a polyaniline in emeraldine form and to make it soluble in various solvents such as toluene, chloroform and tetrahydrofurane (THF) for the purpose of preparing conductor polyaniline films. In this case, the protonating agent acts simultaneously as plasticizer and thereby facilitates the use of the polyanilines in film form or in the form of composite materials.

Reference [3]: Synthetic Metals, 48, 1992, pp. 9197, illustrates the use of another polyaniline protonating agent formed of dodecylbenzenesulphonic acid. As previously, the use of this protonating agent facilitates the use of polyaniline in film form. Although the films obtained in accordance with references [2] and [3] are more resistant to deprotonation, they have mediocre mechanical properties and average conductivity.

Reference [4]: Kulszewicz-Bajer et al., Synthetic Metals, 101, 1999, pp. 713–714, illustrates the use of the di(n-amyl), di(n-decyl), di(butoxy-2-ethyl) and di[2-(butoxy-2-ethoxyl) ethyl] diesters of 5-sulpho-isophtalic acid and the rocanol esters of this 5-sulpho-isophtalic acid as dopants for a polyaniline. However, the polyaniline films doped with these esters obtained from a solution in chloroform have largely insufficient conductivity, in the order of $3.10^{-3}$ S/cm.

It is possible to obtain films having high conductivity, exceeding 300 S/cm for example, by evaporation of a solution containing a polyaniline, camphor sulphonic acid as dopant and metacresol as solvent, as is described in J. Chem. Phys., 103, 22, 1995, pp. 9855–9863 [5].

This solution which appears to be of interest, has the disadvantage that the films contain 12 to 14% by weight of residual meta-cresol which is a toxic product. Another dopant and solvent system such as the 4-ethylbenzene sulphonic acid—hexafluoropropanol system described in reference [6]: Polymer Preprints, 36, 1995, pp. 396–397, leads to a highly conductive film, but the use of this fluorine-containing alcohol on an industrial scale is not possible on account of its toxicity and high cost.

Reference [7]: J. Phys., Condens. Matter, 10, 1998, pp. 8293–8303 describes the use of the system: 2-acrylamido-2-methyl-1-propane sulphonic acid—dichloroacetic acid, with which it is possible to obtain high conductivity. However, the films obtained have low mechanical properties.

Therefore, none of the above-described systems acceptable for use on an industrial scale can be used to obtain simultaneously a polyaniline film having both high conductivity and strong mechanical properties, in particular good flexibility.

The problem is also raised of obtaining conductive composite materials from a mixture of polyaniline with insulating polymers, having both good conductor properties and good mechanical properties.

Reference [8]: Physical Review B, 50, 1994, pp. 13931–13941, and reference [9]: WO-A-98/05040, describe the manufacture of conductor composites containing a polymer host matrix in which a conductor polyaniline is distributed, having extremely low percolation thresholds, less than 1%.

The percolation threshold can be defined as the minimal volume fraction of conductor phase which makes the material conductive on macroscopic scale.

This percolation threshold may be determined using the following formula:

$$\sigma(f) = c(f - f_c)^t$$

in which:
  $\sigma$ represents conductivity,
  c is a constant,
  t is the critical exponent,
  f represents the volume fraction of the conductor phase, and
  $f_c$ is the fraction of conductor phase at the percolation threshold.

In composites with a low percolation threshold, it could be thought that the mechanical properties of the conductor phase should not have too great an effect on the mechanical properties of the composite since this fraction is very low.

However, it is found that the mechanical properties of the composite are deteriorated by the presence of the polyaniline conductor phase, even in systems having a very low percolation threshold. Consequently, it is of great interest to improve the mechanical properties of polyaniline in such composites.

DISCLOSURE OF THE INVENTION

The subject matter of the present invention is precisely the use of new doping agents for polyanilines, with which it is possible to improve the mechanical properties of polyaniline films doped with these agents. These new doping agents act both as plasticizer and as protonating agent. They allow high conductivity levels to be obtained, up to approximately 200 to 300 S/cm of metallic type, and concomitant improvement of the mechanical properties of polyaniline films and of polyaniline-based conductor composites with insulating polymers, in the region of and above the percolation threshold.

Therefore, the subject of the invention is a composition for the manufacture of polyaniline films, made up of a solution, in an organic solvent, of a polyaniline in base emeraldine form and of a dopant formed of a sulphonic or phosphonic acid meeting the formula:

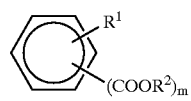

in which:
$R^1$ represents —$SO_3H$ or $PO_3H_2$,
$R^2$ is a linear or branched alkyl group and m is equal to 1 or 2, or
$R^2$ is a group with the formula:

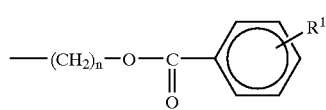

in which $R^1$ is such as defined above and n is a whole number ranging from 1 to 16, and m equals 1, with the exception of the di(n-anyl), di(n-decyl), di (butoxy-2-ethyl) and di [2-(butoxy-2-ethoxy) ethyl] esters of 5-sulphoisophtalic acid and the esters of 5-sulphoisophtalic acid and rocanol.

It also concerns a composition for the manufacture of a conductor composite material containing:
an organic solvent,
a polyaniline in base emeraldine form,
a dopant formed of a sulphonic or phosphonic acid meeting the formula:

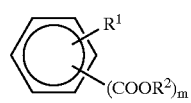

in which:
$R^1$ represents —$SO_3H$ or $PO_3H_2$,
$R^2$ is a linear or branched alkyl group and m equals 1 or 2, or $R^2$ is a group with the formula:

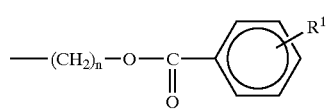

in which $R^1$ is such as defined above and n is a whole number ranging from 1 to 16, and m equals 1,
an insulating polymer, and
a plasticizer for the insulating polymer.

In formula (I), the $R^2$ group is a linear or branched alkyl group, preferably having from 4 to 12 carbon atoms such as to form a hydrophobic group acting as plasticizer and with which it is possible to improve the solubility of the polyanilines in organic solvents.

As an example of a group which may be used, the 2-ethyl-hexyl group may be cited.

If m equals 2, these phosphonic or sulphonic acids correspond to esters of phtalic, isophtalic and terephtalic acids functionalised with an acid group of —$SO_3H$ or —$PO_3H_2$ type.

If m equals 1, they are benzoates functionalised on the aromatic cycle by the above-cited acid groups or they are dibenzoates also functionalised by acid groups and meeting the formula:

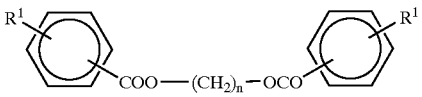

By way of example, the sulphonic acid may meet the formula:

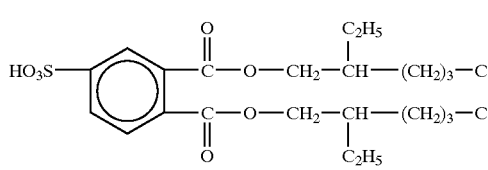

These sulphonic or phosphonic acids may be prepared from corresponding functionalised phtalic or benzene acids meeting the formula:

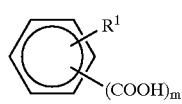

in which $R^1$ and m are such as defined above by esterification of these acids using an alcohol of formula $R^2OH$ in which $R^2$ is such as defined above.

The acids of formula (IV) used as starting products in this method are commercially available products or may be prepared by sulphonation or phosphorylation of phtalic acids or of benzene acid.

If $R^2$ represents the group of formula (II) and m equals 1, the sulphonic or phosphonic acid may be prepared in the same way by esterification of the acid of formula (IV) with the corresponding $R^2OH$ alcohol in which $R^2$ is the group of formula (II), or alternatively by condensation of two molecules of formula (IV) in which m=1, with a diol of HO—$(CH_2)_n$,—OH type.

The sulphonic and phosphonic acids described above have good properties as protonating agent on account of the $SO_3H$ or $PO_3H_2$ group, and as plasticizer and solubilising agent through the presence of the group:

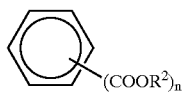

Therefore, they may be used in compositions for the manufacture of polyaniline films.

In the compositions of the invention, the role of the functionalised dopant of formula (I) is to improve the mechanical properties and more particularly the flexibility of the films or deposits obtained from the composition by evaporation of the solvent.

The polyaniline used in this composition is in base emeraldine form. It may be prepared by conventional oxidizing polymerisation or by enzymatic polymerisation, or by other methods such as electrochemical polymerisation. Base emeraldine meets the formula:

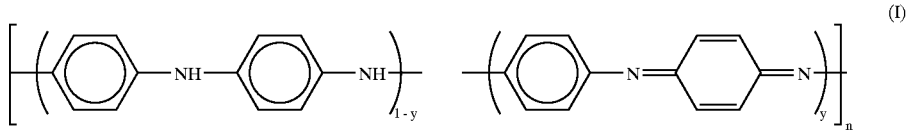

where y=0.5.

It is specified that, according to the invention, by polyaniline is meant not only the polyanilines obtained by polymerisation of aniline, but also the polyanilines obtained from aniline substituted on the cycle or on nitrogen.

The solvents used in these compositions may be of various types, but preference is given to non-toxic, inexpensive solvents which do not have a propensity to remain within the matrix of the polyaniline film after pouring and evaporation of the solvent.

Therefore, as solvent, preferential use is made of halogenated derivatives of a carboxylic acid having the formula:

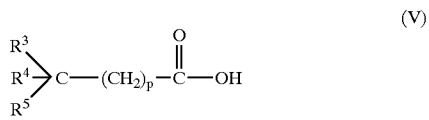

in which $R^3$, $R^4$ and $R^5$, which may be identical or different, represent H or a halogen atom chosen from among F, Cl and Br, at least one of $R^3$, $R^4$ and $R^5$ representing a halogen atom, and p equals 0.

in which $R^3$, $R^4$ and $R^5$, which may be identical or different, represent H or a halogen atom chosen from among F, Cl and Br, at least one of $R^3$, $R^4$ and $R^5$ representing a halogen atom, and p equals 0.1 or 2.

When the derivatives meeting formula (V) contain 2 or 3 halogen atoms, the latter may evidently be different.

As an example of solvents which may be used, mention may be made of dichloroacetic, difluoroacetic, α-trifluoroacetic, chlorodifluoracetic, 2-chloropropionic, 2-bromobutyric and 2,2-dichloro-propionic acids.

In the compositions of the invention for the manufacture of conductor polyaniline films, the polyaniline and dopant contents of the solution are such that the molar ratio of the dopant to the polyaniline in base emeraldine form lies within the range of 0.4 to 0.6.

This ratio is calculated on the basis of a molar mass of base emeraldine corresponding to a monomer motif of emeraldine which is 90.5 g. The polyaniline content of the solution generally lies within the range of 0.1 to 1% by weight.

Should high concentrations be used, the storage time for the solution must be shortened in order avoid gelling.

To prepare a polyaniline film from this composition, the solution is poured onto a carrier and the solvent is evaporated. The carrier may be left in place or a self-supporting film may be made by separating it from the carrier.

A further subject of the invention is a composition for the production of polyaniline-based conductor composite materials, which contains:

an organic solvent a polyaniline in base emeraldine form, a dopant made up of a sulphonic or phosphonic acid of formula (I) described above, an insulating polymer, and a plasticizer for the insulating polymer.

In this composition, the dopants and the organic solvents used are identical to those cited for the composition used to produce polyaniline films.

The polyaniline and dopant concentrations in the solution also lie within the same ranges.

In this composition, the role of the functionalised dopant is not only to improve the mechanical properties, flexibility in particular, but also to lower the percolation threshold of the composite material containing polyaniline and an insulating polymer.

The insulating polymers used may be of different types. By way of example, polystyrene may be cited, or polymethylmethacrylate, cellulose polymers, polyvinylchloride, polycarbonates, polyesters and polyurethanes.

In this composition, a plasticizer for the insulating polymer is also used. Conventional plasticizers may be used such as the diesters of phtalic acids, the diesters of dicarboxylic acids or the triesters of phosphoric acid.

The choice of these plasticizers allows further lowering of the percolation threshold of the composite material.

The plasticizer and insulating polymer contents of the composition are chosen such as to obtain satisfactory conductivity of the composite material.

Generally, the composition is prepared by mixing a first solution of the polyaniline and dopant in the solvent with a second solution in the same solvent of the insulating polymer and plasticizer.

The polyaniline and dopant concentration in the first solution is generally from 0.1 to 1% by weight.

The concentration of insulating polymer and plasticizer in the second solution is generally from 5 to 10% by weight, and the ratio of the plasticizer content over the insulating polymer content is generally from 20 to 45% by weight.

To prepare the composition, the two solutions are mixed for sufficient time to obtain good homogeneity.

To prepare the composite material, the said composition is then poured to form a film and the solvent is slowly evaporated.

Evaporation may be conducted at room temperature or at a higher temperature, for example from 25 to 40° C. in a nitrogen atmosphere.

Generally, the quantities of mixed solutions are such that after evaporation of the solvent a composite material is obtained containing:
 a) 0.06 to 10% by weight polyaniline and dopant,
 b) 55 to 99.9% by weight of insulating polymer, and
 c) up to 44.94% by weight of plasticizer for the insulating polymer.

Other characteristics and advantages of the invention will become better apparent on reading the following examples, evidently given for illustration purposes and therefore non-limitative, with reference to the appended drawings.

Figure 1:
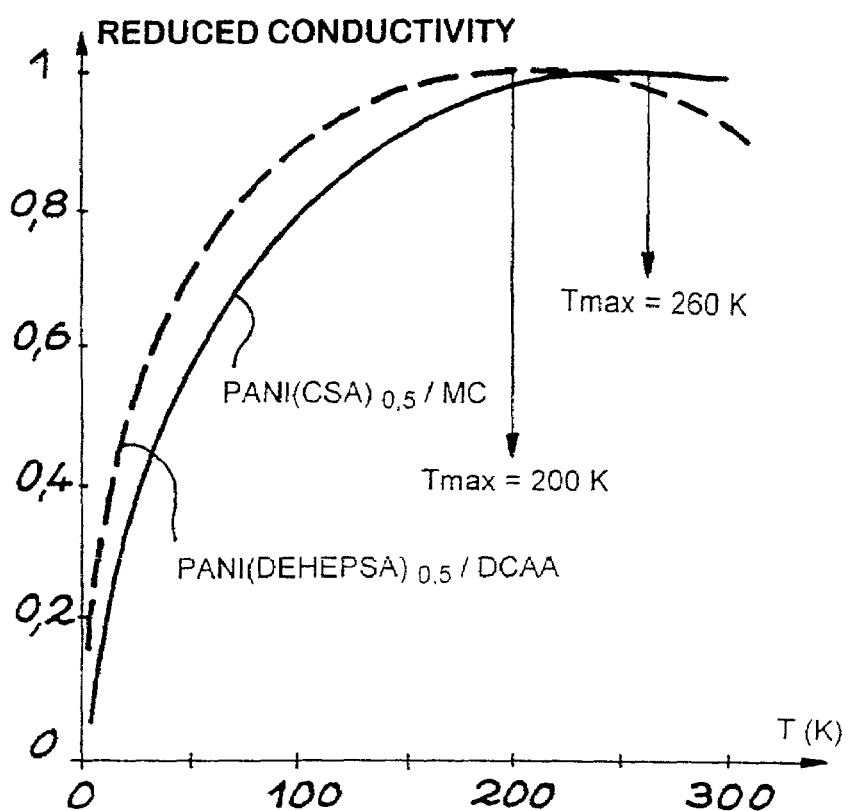
FIG. 1 illustrates the variations in reduced conductivity of a polyaniline film of the invention PANI (DEHEPSA)$_{0.5}$/DCAA and of a polyaniline film of the prior art PANI(CSA)$_{0.5}$/MC in relation to temperature (in K).

Figure shows the stress/strain curves of a polyaniline film of the invention PANI(DEHEPSA)$_{0.5}$/DCAA and of a polyaniline film of the prior art PANI(CAS)$_{0.5}$/MC.

DETAILED DESCRIPTION OF EMBODIMENTS

The following examples illustrate the use of the di-2-ethylhexyl ester of 1,2-benzene dicarboxylic-4-sulphonic acid, that is to say the sulphonic acid of formula (III) as dopant for the production of polyaniline films and of polyaniline-containing composite material films.

EXAMPLE 1

In this example, a highly conductive, self-supporting polyaniline film according to the invention is prepared which has excellent mechanical properties, flexibility properties in particular. The doping agent used is the di-2-ethylhexyl ester of 1,2-benzene dicarboxylic-4-sulphonic acid, that is to say the sulphonic acid of formula (III).

With this dopant, it is possible to make the base emeraldine polyaniline conductive.

A) Preparation of Base Emeraldine

Base emeraldine is prepared according to a modified version of the method described in the publication by P. M. Beadle, Y. F. Nicolau, E.Bank, P. Rannou and D. Djurado in Synthetic Metals, 95, 1998 pp. 29–45 [10]. The reaction is conducted at −27° C.

Firstly, an aniline solution is prepared in a mixture of water-alcohol-HCl and LiCl. The exact composition is as follows: 10 ml (0.1097 mole) aniline, 85 ml 3M HCl solution, 95 ml ethanol and 16 g LiCl. To this solution is added the solution containing the oxidant, previously cooled to −27° C., whose composition is the following: 6.25 g (0.0274 mole) ammonium persulphate, 60 ml 2M HCl solution and 8 g LiCl. The reaction is carried out while making permanent measurements of temperature and solution potential. After approximately 2 hours, a reducing solution is added made up of 3.64 g (0.0183 mole) FeCl2, 5 g LiCl and 50 ml 2M HCl to better control the oxidation state of the polyaniline. After 1 additional hour, the reaction is halted by separating the precipitated polymer, either by centrifugation or by filtration. The precipitate is washed several times in distilled water and then in methanol, and it is finally dried until a constant mass is obtained. The emeraldine salt so obtained is then converted to base emeraldine by treatment in 2 liters of aqueous 0.3M NH$_3$ solution for 48 hours. The base emeraldine is then rinsed in 5 to 6 liters of distilled water, then in 2 liters of methanol and it is dried until a constant mass is obtained.

In the following step, the fractions of low molecular weight are removed by successive methanol and chloroform exactions using a Soxhlet apparatus. The inherent viscosity of the base emeraldine so obtained in a solution at 0.1% by weight in 98% sulphuric acid is 2.25 dl/g.

b) Preparation of the di-2-ethylhexyl ester of 1,2-benzene dicarboxylic-4-sulphonic acid.

6.3 g (25.6 mmole) of 4-sulphophtalic acid in the form of a 50% by weight aqueous solution is mixed with 10 g (76.8 mmole) of 2-ethyl-1-hexanol at room temperature under a stream of nitrogen. The temperature of the mixture is raised to 110–120° C. The reaction is continued at this temperature for 2 to 3 hours and the water produced in the reaction is constantly removed by distillation. The reaction mixture is then poured into an aqueous solution of 1M HCl. After 5 to 10 min, the mixture separates into two phases. The organic phase is collected and washed 3 times with an aqueous 1M HCl solution. The product is then ether extracted. After evaporation of the ether and volatile impurities, the product is dried on MgSO4. Finally, the product is identified and characterized by elementary analysis, IR spectroscopy, mass spectroscopy and proton NMR.

C) Preparation of the Self-Supporting, Highly Conductive Polyaniline Film.

140 g of base polyaniline are mixed with 369 mg of the di-2-ethylhexyl ester of 1,2-benzene dicarboxylic-4-sulphonic acid (DEHEPSA) with 48 ml dichloroacetic acid (DCAA). The mixture is shaken vigorously at room temperature for 4 to 5 days until no further changes in the UV-Vis-NIR spectrum are seen to occur. The solution formed is filtered on a 0.45 μm microfilter. A film is poured from this solution by evaporation at 40° C. under a stream of nitrogen. The film obtained is rinsed in water and it is vacuum dried at 50° C. The film has excellent flexibility: it can be bent several times without undergoing any degradation. Elementary analysis shows that the film no longer contains any solvent. Its conductivity, measured by a 4-contact method, is typically 100 to 200 S/cm at room temperature.

In FIG. 1, the variations are shown in relation to temperature (in K) of the reduced conductivity of the film obtained in this example called PANI (DEHEPSA)$_{0.5}$/DCAA and of the film PANI(CSA)$_{0.5}$/MC obtained according to the prior art (reference [5]) using camphor sulphonic aicd (CSA) as dopant and m-cresol (MC) as solvent.

Reduced conductivity is the conductivity divided by maximum conductivity, which in the tested PANI(DEHEPSA)$_{0.5}$/DCAA sample is 100 S/cm, and in the PANI (CSA)$_{0.5}$/MC sample is 250 S/cm.

In both cases the metallic character will be noted at high temperature: drop in conductivity when temperature increases. Also, it can be seen that the maximum lies at a temperature Tmax that is lower (200K) for the PANI(DEHEPSA)$_{0.5}$/DCCA film than for the film of the prior art PANI(CSA)$_{0.5}$/MC for which it is 260 K.

Therefore, the conductivity of the polyaniline film of the invention is of metallic type.

Figure 2:
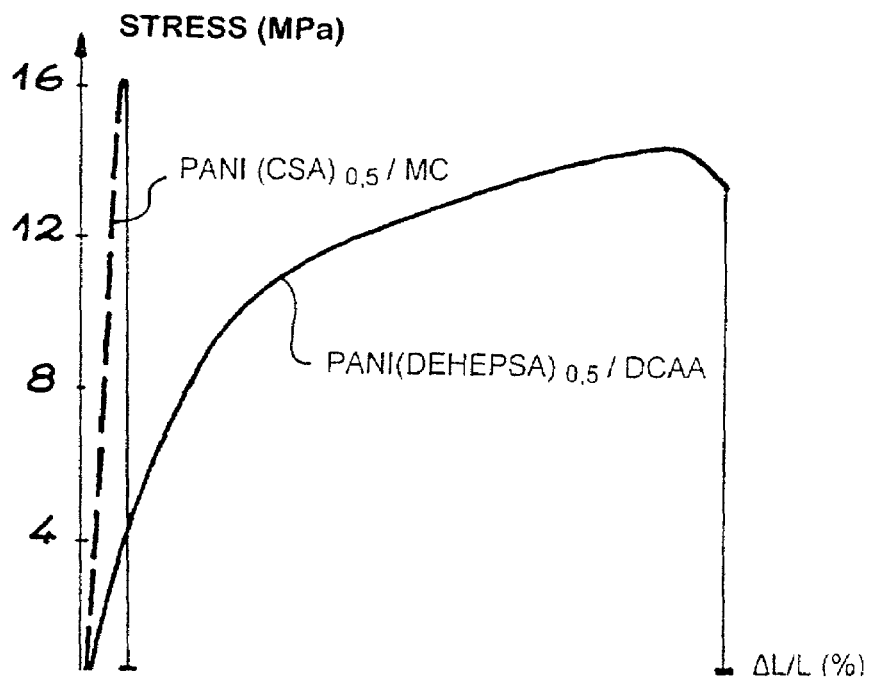

FIG. 2 shows the stress(MPa)/strain ($\gamma$L/L as a %) curves of the PANI(DEHEPSA)$_{0.5}$/DCAA and PANI (CSA)$_{0.5}$/MC films obtained during tests in which the film is regularly elongated at a constant speed of 1 mm/min, and the stress to be applied to the film is measured.

With the PANI(DEHEPSA)$_{0.5}$/DCAA film of the invention, a factor of over 10 is gained for elongation to fracture, which demonstrates the much greater pliability of the film.

COMPARATIVE EXAMPLE 1

The same operating mode is followed as in example 1 to prepare the solution, except that camphorsulphonic acid is used as doping agent instead of the di-2-ethylhexyl ester of 1,2-benzene dicarboxylic-4-sulphonic acid, in the same molar ratio of doping agent/polyaniline mother. A film having conductivity of much the same order is obtained but its mechanical properties are distinctly poorer. In particular, it breaks on bending.

COMPARATIVE EXAMPLE 2

The same operating mode is followed as in example 1 to prepare a solution, except that m-cresol is used as solvent instead of dichloroacetic acid. A film having more or less similar conductivity is obtained, however 10 to 15% by weight of solvent subsists in the film even after extended pumping. The residual m-cresol is the cause of the film's unpleasant smell. In addition, on account of the slow release of the solvent, the mechanical and electric properties of the film change over time.

EXAMPLE 2

In this example, a highly conductive selfsupporting film of polyaniline is prepared, the polyaniline being doped with the di-2-ethylhexyl ester of 1,2 benzene dicarboxylic-4-sulphonic acid following the same operating mode as in example 1. But the dichloroacetic acid is replaced by chlorodifluoroacetic acid. After pouring, a pliable film is obtained whose conductivity, measured using the standard 4-point technique, is 100 S/cm.

EXAMPLE 3

In this example, a polyaniline-based conductor composite film is prepared in accordance with the invention, using polymethylmethacrylate as insulating polymer. The base emeraldine polyaniline and doping agent are prepared following the same operating mode as in example 1.

a) Preparation of the Polymethylmethacrylate and Plasticizer Solution in Dichloroacetic Acid 5 ml of solution are prepared by mixing 1 g polymethylmethacrylate and 0.35 g dibutylphtalate with dichloroacetic acid under vigorous shaking.

b) Preparation of the Conductor Composite Material 0.5 ml of the polymethylmethacrylate and plasticizer solution are mixed in dichloroacetic acid with 0.683 ml dichloroacetic solution containing 2.14 mg base emeraldine and 5.56 mg of the di-2-ethylhexyl ester of 1,2-benzene dicarboxylic-4-sulphonic acid. The mixture is homogenized by vigorous shaking.

Films are poured from this mixture by slow evaporation of the dichloroacetic acid at 40° C. The base emeraldine content of the dry films is 1.5% by weight.

The conductivity of the films obtained, measured using the standard four-point technique, is 0.55 S/cm.

COMPARATIVE EXAMPLE 3

The same operating mode is followed as in example 3 to prepare a composite material from the same solutions, except that no plasticizer (dibutylphtalte) is added. The conductivity of the films obtained, having a base emeraldine content of 1.5% by weight, is 0.05 S/cm, that is to say an order of magnitude that is smaller than the value obtained in example 3.

CITED REFERENCES

[1] Synthetic Metals, 21, 1987, pp. 21–30.
[2] Polymer, 34, N° 20, 1993, pp. 4235–4240.
[3] Synthetic Metals, 48, 1992, pp. 91–97.
[4] Kulszewicz-Bajer et al., Synthetic Metals, 101, 1999, pp. 713–714.
[5] J. Chem. Phys., 103, 22, 1995, pp. 9855–9863
[6] Polymer preprints, 36, 1995, pp. 396–397
[7] J. Phys.: Condens. Matter, 10, 1998, pp. 8293–8303
[8] Physical Review B, 50, 1994, pp. 13931–13941.
[9] WO-A-98/05040
[10] P. M. Beadle, Y. F. Nicolau, E. Banka, P. Rannour & D. Djurado in Synthetic Metals, 95, 1998, pp. 29–45.

The invention claimed is:

1. Composition for the manufacture of polyaniline films, made up of a solution, in an organic solvent, of a polyaniline in base emeraldine form and of a dopant formed of a sulphonic or phosphonic acid, having the formula:

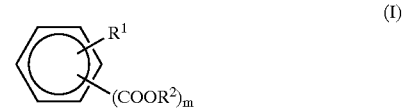

(I)

in which:

R$^1$ represents —SO$_3$H or —PO$_3$H$_2$

R$^2$ represents:

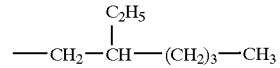

and m equals 2, in which case said sulphonic or phosphonic acid meets the formula:

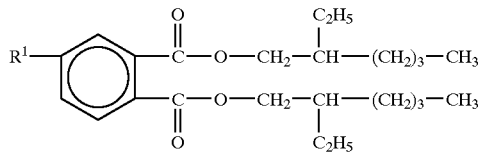

or
R² is a group having the formula:

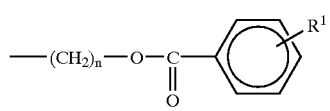

in which R¹ represents —SO₃H or —PO₃H₂, n is a whole number ranging from 1 to 16, and m equals 1.

2. Composition according to claim 1, in which the solvent is a halogenated derivative of a carboxylic acid having the formula:

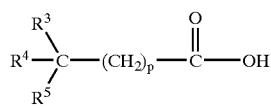

In which $R^3$, $R^4$ and $R^5$, which are identical or different, represent H or a halogen atom chosen from among F, Cl and Br, at least one of $R^3$, $R^4$ and $R^5$ representing a halogen atom, and p equals 0, 1 or 2.

3. Composition according to claim 2, in which the solvent is chosen from among dichloroacetic, trifluoroacetic, difluoroacetic, chlorodifluoroacetic, 2-chloropropionic, 2-bromobutyric and 2,2-dichloro-proprionic acids.

4. Composition according to claim 1, in which the sulphonic acid meets the formula:

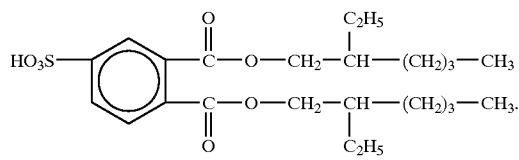

5. Composition according to claim 4, in which the solvent is dichloro-acetic acid.

6. Composition according to claim 1, in which the polyaniline and doping agent contents in the solution are such that the molar ratio of the doping agent to the polyaniline in base emeraldine form lies within the range of 0.4 to 0.6.

7. Composition according to claim 1, in which the polyaniline content of the solution is 0.1 to 1% by weight.

8. Composition for the manufacture of a conductor composite material containing:
an organic solvent,
a polyaniline in base emeraldine form,
a doping agent formed of a sulphonic or phosphonic acid, meeting the formula:

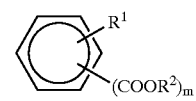

in which:
$R^1$ represents —SO₃H or —PO₃H₂,
$R^2$ represents:

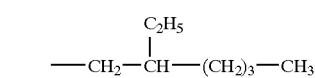

and m equals 2, in which case said sulphonic or phosphonic meets the formula:

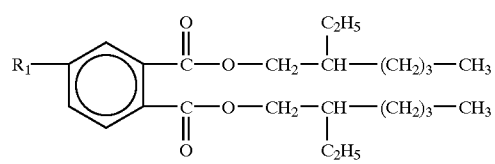

R² is a group having the formula:

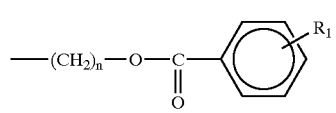

in which $R^1$ represents —SO₃H or —PO₃H₂, n is a whole number ranging from 1 to 16, and m equals 1,
an insulating polymer, and
a plasticizer for the insulating polymer.

9. Composition according to claim 2, in which the solvent is a halogenated derivative of a carboxylic acid having the formula:

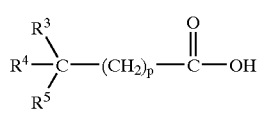

in which $R^3$, $R^4$, and $R^5$, which are identical or different, represent H or a halogen atom chosen from among F, Cl and Br, at least one of $R^3$, $R^4$, and $R^5$ representing a halogen atom, and p equals 0, 1 or 2.

10. Composition according to claim 9, in which the solvent is chosen from among dichloroacetic, trifluoroacetic, chlorodifluoroacetic, 2-chloropropionic, 2-bromobutyric and 2,2-dichloro-proprionic acids.

11. Composition according to claim 8, in which the sulphonic acid meets the formula:

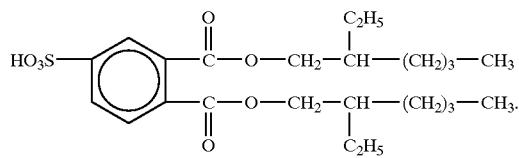

(III)

12. Composition according to claim 11, in which the solvent is dichloro-acetic acids.

13. Composition according to claim 8, in which the polyaniline and doping agent contents in the solution are such that the molar ratio of the doping agent to the polyamine in base emeraldine form lies within the range of 0.4 to 0.6.

14. Composition according to claim 8, in which the polyamine content of the solution is 0.1 to 1% by weight.

15. Composition according to claim 8, in which the insulating polymer is chosen from among polystyrene, polymethylmethacrylate, cellulose polymers, polyvinylchloride, polycarbonates, polyesters and polyurethanes.

16. Composition according to claim 8, in which the plasticizer is chosen from among the diesters of phthalic acids, the diesters of phtalic acids, the diesters of dicarboxylic acids and the triesters of phosphoric acid.

17. Method for manufacturing a conductor composite material containing a polyaniline, characterized in that it comprises the following steps:
   preparing a composition according to claim 8, and
   forming the conductor composite material from said composition by evaporation of the solvent.

18. Method according to claim 17, characterized in that the composition is prepared by mixing a first solution of polyaniline and dopant in the solvent with a second solution in the same solvent of the insulating polymer and of the plasticizer.

19. Electricity conductive composite material containing a matrix of insulating polymer in which a conductor polyaniline is distributed doped with a sulphonic or phosphonic acid, meeting the formula:

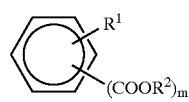

(I)

in which:
  $R^1$ represents —$SO_3H$ or $PO_3H_2$,
  $R^2$ represents:

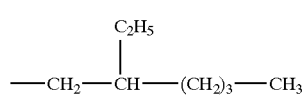

and m equals 2, in which case said sulphonic or phosphonic acid meets the formula:

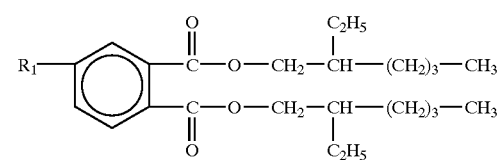

$R^2$ is a group having the formula:

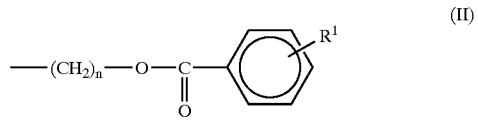

(II)

in which $R^1$ represents —$SO_3H$ or $PO_3H_2$, n is a whole number ranging from 1 to 16, and m equals 1, and a plasticizer for the insulating polymer.

20. Composite material according to claim 19, in which the insulating polymer is polymethylmethacrylate.

21. Composite material according to claim 19, which contains:
   a) 0.06 to 10% by weight polyaniline and dopant,
   b) 55 to 99.9% by weight insulating polymer, and
   c) up to 44.94% by weight of plasticizer for the insulating polymer.

22. Polyaniline film, doped with a sulphonic or phosphonic acid, meeting the formula:

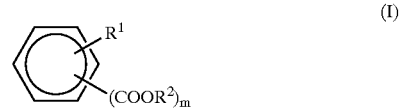

(I)

in which:
  $R^1$ represents —$SO_3H$ or $PO_3H_2$,
  $R^2$ represents:

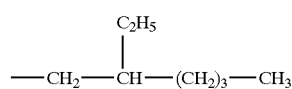

and m equals in which case said sulphonic or phosphonic acid meets the formula

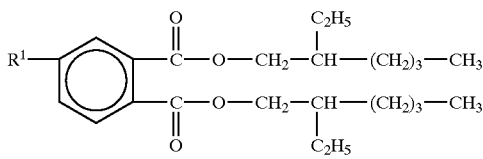

or

R² is a group having the formula:

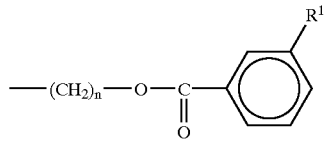
(II)

in which R¹ represents —SO₃H or PO₃H₂, n is a whole number ranging from 1 to 16, and m equals 1.

23. Polyaniline film according to claim 22, doped with sulphonic acid having the formula:

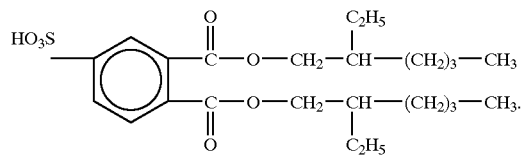
(III)

24. Composition for the manufacture of polyaniline films, made up of a solution, in an organic solvent, of a polyaniline in base emeraldine form and of a dopant formed of a diester of 4-sulfophthalic acid, having the formula:

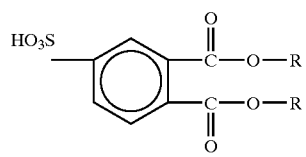

in which:

—R represents a group selected among the n-pentyl, n-octyl, n-decyl, n-dodecyl, 2-ethylhexyl, butoxyethyl and butoxyethoxyethyl groups.

* * * * *